(12) United States Patent
Kunin

(10) Patent No.: US 8,647,682 B2
(45) Date of Patent: Feb. 11, 2014

(54) COMPOSITION AND METHOD FOR TREATING KERATOSIS PILARIS

(76) Inventor: Audrey Kunin, Mission Hills, KS (US)

( * ) Notice: Subject to any disclaimer, the term of this patent is extended or adjusted under 35 U.S.C. 154(b) by 645 days.

(21) Appl. No.: 11/428,000

(22) Filed: Jun. 30, 2006

(65) Prior Publication Data

US 2008/0003188 A1    Jan. 3, 2008

(51) Int. Cl.
*A61K 36/00*    (2006.01)

(52) U.S. Cl.
USPC ............................................................ 424/725

(58) Field of Classification Search
None
See application file for complete search history.

(56) References Cited

U.S. PATENT DOCUMENTS

| 2003/0026794 A1* | 2/2003 | Fein ............................. 424/94.2 |
| 2003/0118623 A1* | 6/2003 | de Paoli Ambrosi .......... 424/401 |
| 2004/0191196 A1* | 9/2004 | Tamarkin ........................ 424/62 |

FOREIGN PATENT DOCUMENTS

JP    2002284697 A    *    10/2002

OTHER PUBLICATIONS

DERMAdoctor KP Duty Dermatologist Moisturizing Therapy for Dry Skin. Internet Archive Date: May 2, 2004 [Retrieved from the Internet on: Nov. 30, 2008]. Retrieved from: <http://web.archive.org/web/20040502223241/www.aaaskindoctor.com/ke.html>.*

"Benefits of White tea". Article Date: Feb. 13, 2006. Web Archive Date: Apr. 19, 2006 [Retrieved from the internet on: Aug. 23, 2009]Retrieved from: <http://web.archive.org/web/20060419083617/http://www.disabled-world.com/artman/publish/white_tea.shtml>.*

"Joie de Vie" Internet Archive date: Jun. 2, 2005 [Retrieved from the Internet on: Nov. 30, 2010]. Retrieved from the Internet: <URL: http://web.archive.org/web/20050602090803/www.joiedevie.com/products-bodyproducts.htm>.*

* cited by examiner

*Primary Examiner* — Amy L Clark
(74) *Attorney, Agent, or Firm* — Husch Blackwell LLP

(57) ABSTRACT

A combination comprising buffered glycolic acid, urea, and white tea extract for treating keratosis pilaris is provided. The improved composition provides a significant and unexpected reduction of KP symptoms when applied topically to an affected area.

15 Claims, 3 Drawing Sheets

Keratosis Pilaris

1. _____ mm
2. Erythema

3. _____ mm

4. Inflammation

Very Inflamed

KERATOSIS PILARIS
IMAGE ANALYSIS

METHODS

Equipment

PC: IBM compatible Pentium III 500Mhz with math co-processor and 256 mb memory running under Windows 2000.

Video: Cohu solid state B&W camera, 50mm lens/30mm extension, Coreco Ultra II frame grabber.

Software: OPTIMAS v6.5, Microsoft EXCEL, StatSoft STATISTICA.

Lighting: A focused light source (arrow in diagrams below) directed at a 25° angle from the plane of the replica.

Principle

The goal of the analysis is to isolate the texture due to the Keratosis Pilaris (KP) "Bumps". Each KP "Bump" produces a small well in the negative replica. The shadow produced by the oblique lighting of one of these wells is shone diagrammatically in the TOP VIEW below. For each well there is a more or less crescent shaped shadow on the "falling side of the well" and a crescent shaped highlight in the "rising" side of the well. By analyzing the number and size of the shadows, information about the bumps is collected.

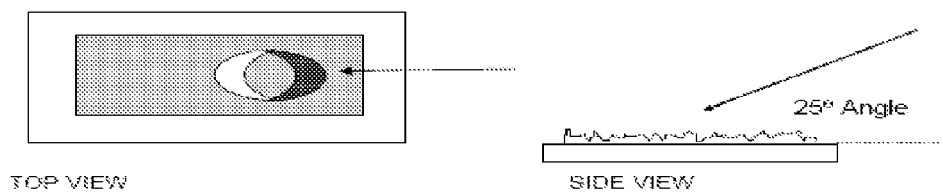

TOP VIEW                SIDE VIEW

Figure 3

KERATOSIS PILARIS
IMAGE ANALYSIS

WELL ANALYSIS

The "well" is a rounded depression in the skin replica. The dimension of the shadow measured normal to the incident light direction (Height) is a measure of the well diameter, the dimension parallel to the incident light direction (Breadth) is a measure of the well depth. A typical portion of an image is shown below.

The data consists of the mean Diameter, Depth, and Area of wells from the detected shadows as well as the total number detected in the sampling area. These parameters relate to the size and number of the actual skin lesion at the test site. The severity of KP can be estimated by calculating the number, area, breadth and height of the detected shadows in a standard (approximately 15mm x 45 mm) field of the image.

Breadth ≈ Depth of well

Height ≈ Diameter of well

Dark shadow (on right) and bright face (on left) in a well produced by a KP bump.

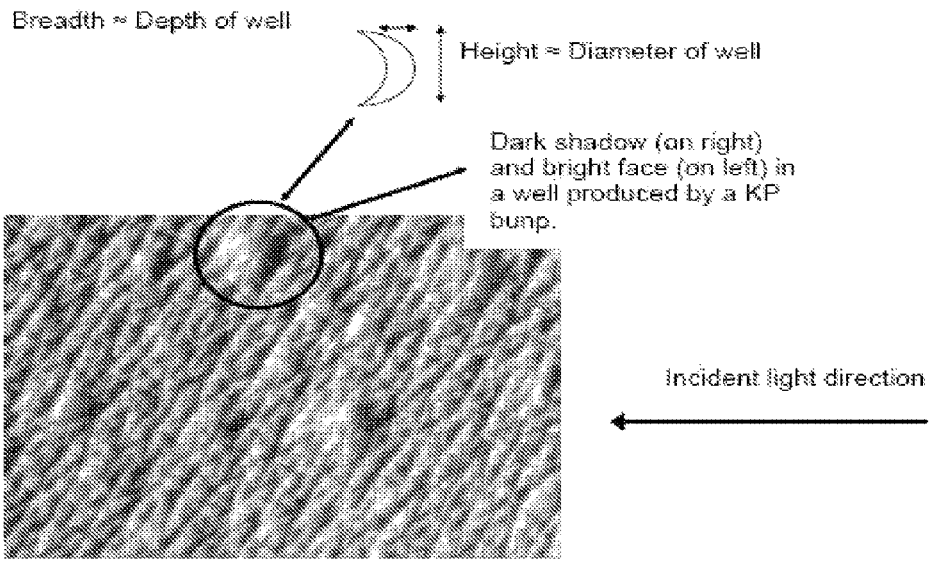

Incident light direction
←

COMPOSITION AND METHOD FOR TREATING KERATOSIS PILARIS

BACKGROUND OF THE INVENTION

Keratosis pilaris (hereinafter KP) is a genetic dermatologic condition that affects the keratinization process. The keratinization process is responsible for the formation of epidermal skin cells. KP causes hyperkeratosis, wherein surplus epidermal skin cells form around individual hair follicles. As the epidermal skin cells build up, normal hair growth is inhibited. The individual hairs are unable to reach the surface as they become trapped beneath the cell debris. KP primarily affects the upper lateral arms, lateral thighs, buttocks, upper back and facial cheeks. During and following puberty, KP can be a contributing factor to the development of follicular acne, and is frequently associated with other skin disorders including atopic dermatitis or ichthyosis vulgaris. It is estimated that as many as fifty percent of the worldwide population is affected to some degree by KP.

The surface of healthy skin is substantially smooth. KP distorts the normally smooth epidermal surface as follicular papules form causing raised rough patches. The skin may have an uneven nutmeg-grater appearance, and include xerosis, inflammation, redness and potentially associated acne or razor bumps. Skin discoloration, dependent on the individual's skin tone, may be pink, purple, red, brown or black polka dots that form beneath miniature mounds of keratin debris. Seasonal fluctuations can be seen, with improvement more likely during the summer.

KP is extremely noticeable, to the point of causing significant psychological concern to affected patients, who tend to alter their habits to minimize public skin exposure. Conventional KP treatments consist essentially of offering topical exfoliants to smooth skin, or physical treatment to smooth skin such as microdermabrasion or the use of cleansing scrubs, in combination with topical moisturizers or humectants to hydrate skin. While the skin may temporarily become smoother with these methods, no known methods target the inflammation at the base of individual hair follicles. Therefore, even patients responsive to conventional treatments continue to be affected by significant visible polka dotting of their skin.

There exists therefore a need for a KP treatment of that effectively addresses all aspects of the physiology of the condition, thereby providing significant improvement in KP symptoms.

SUMMARY OF THE INVENTION

In one of many illustrative aspects of the present invention, there is provided an improved composition for treating KP, the improved composition comprising buffered glycolic acid, urea and at least one tea extract.

In another illustrative aspect of the present invention there is provided a method of making the improved composition of the present invention.

In yet another illustrative aspect of the present invention there is provided a method of treating KP, the method comprising topically administering to an affected area a non-toxic effective dosage of the improved composition.

BRIEF DESCRIPTION OF THE SEVERAL VIEWS OF THE DRAWINGS

FIG. 2 illustrates a method of lighting and assessing skin to determine severity of KP symptoms; and FIG. 3 illustrates the well analysis method of assessing skin to determine severity of KP symptoms.

DETAILED DESCRIPTION OF THE INVENTION

Figure 1:
FIG. 1 illustrates scales used to assess KP, erythema and inflammation.
Figure 1:
Figure 1:
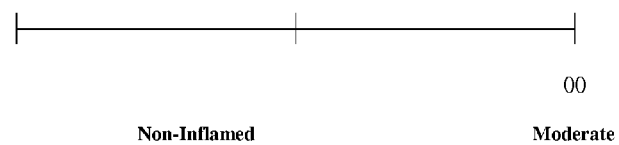

There is provided a novel combination of buffered glycolic acid, urea and at least one tea extract. The resulting improved composition provides a significant and unexpected reduction of KP symptoms when applied topically to an affected area. The improved composition was evaluated by clinical grading of overall keratosis pilaris, mediscope photography, Mediscope D-Scope II imaging, mage analysis of Silflo™ replicas and corneometer measurements. These evaluations demonstrated efficacy of the improved composition to significantly diminish the appearance of keratosis pilaris by decreasing inflammation of the hair follicles and increasing skin hydration.

Glycolic acid is an alpha hydroxy acid (AHA), the simplest of a variety of fruit acids useful as chemical exfoliants and skin lighteners. Glycolic acid has an excellent capability to penetrate the skin, and is isolated from sugar cane, sugar beets and unripe grapes. In the present improved composition, it is preferred that the glycolic acid be buffered to a pH of about 3.0 to about 4.5.

Urea, also known as carbomide, promotes rehydration and is therefore typically utilized as a skin softener. Urea is also thought to increase the solubility of proteins by disrupting non-covalent bonds.

Tea extracts, primarily green and white tea, are strong antioxidants.

It has been determined that an effective combination of the improved composition comprises from about 0.01% to 60% buffered glycolic acid, from about 0.01% to 50% urea, and at least 0.01% of green tea extract, white tea extract or mixtures thereof; with from about 5% to 20% buffered glycolic acid, from about 1.0% to 10% urea, and at least 1% green tea extract, white tea extract or mixtures thereof being preferred; and about 12% buffered glycolic acid, about 5% urea, and about 5% green tea extract, white tea extract or mixtures thereof being even more preferred.

In an alternative embodiment, the improved composition of the present invention further includes from about 0.01% to 30.0% salicylic acid, from about 0.01% to 30% azelaic acid and from about 0.01% to 30% lactic acid; with from about 0.1% to 5% salicylic acid, from about 0.1% to 5% azelaic acid and from about 0.1% to 5% lactic acid being preferred; and about 2% salicylic acid, about 1% azelaic acid and about 3% lactic acid being even more preferred.

The improved composition may include additional components without departing from the scope of the present invention. These components may be over the counter or prescription drugs, in various strengths as are known and pharmaceutically acceptable, depending on the desired ultimate formulation of the improved composition. It is further noted that the term "acid" includes pharmaceutically acceptable salts thereof.

These components may include additional AHA exfolients, including lactic acid, malic acid and tartaric acid, as well as other organic acids including, for example, oleanolic acid.

Additional skin lightening agents may be added to the improved composition to address the skin discoloration issues attendant to KP. Skin lighteners are well known in the art, and include AHAs, beta hydroxy acids, retinoids and other Vitamin A derivatives including tretinoin, iso-treninoin, retinol, retinyl palmitate, retinoic acid, tazarotene and adapalene, all of which work to exfoliate the skin. These acids help smooth the skin, attract moisture to the skin and aid in evening texture and complexion. In addition, sutilains, including agents like papain, dissolve the intercellular cement, effectively dissolving the bonds that hold the cells together.

Other skin lightening agents include components that inhibit tyrosinase, an enzyme critical to the formation of melanin. Excess melanin, produced by hyperactive melanocytes, is responsible for skin darkening or discoloration. Hydroquinone, resorcinol, mitracarpus scaber extract (mulberry extract and its active ingredient hauronoside), arctostaphylos uva ursi leaf extract (bearberry and its active ingredient arbutin), kojic acid and kijic acid dipalmitate all act as tyrosinase inhibitors. Dithiaoctanediol prevents the enzymatic activation of tyrosinase by blocking enzyme glycosylation. Licorice extract (glabridin) inhibits pigmentation by preventing tyrosinase activation, and is purported to be an anti-inflammatory. Beta carotene blocks tyrosinase receptors. Gluconic acid acts as a chelating agent, binding the copper molecules necessary for tyrosinase activation. Azeleic acid is a naturally occurring byproduct of a yeast metabolism that works selectively on overactive melanocytes. Vitamin C, Vitamin C derivatives including Vitamin C esters, L-ascorbic acid, magnesium ascorbyl phosphate and sodium ascorbyl phosphate, prevent melanin formation. Finally, although the mechanism is not known, anecdotal evidence exists of skin lightening by melatonin.

The improved composition of the present invention includes at least one antioxidant selected from green tea extract, white tea extract and mixtures thereof. Several additional organic acids also known for their antioxidant activity, including AHAs, as well as superoxide dismutase, roobios tea and lycopene, are suitable for inclusion in the improved composition. Additional vitamins, including vitamin K, herbs, minerals, including selenium aspartate, and essential oils, such as tree oil, may also be added to the formulation.

Additional active ingredients that may be included in the improved composition include steroid or steroidal compounds, including hydrocortisone and prednisone, known for decreasing inflammation. Immunosuppressants, including Prograf®, Cyclosporin/Neoral®, Imuran®, Cellcept®, topical sirolimus, pimicrolimus, and tacrolimus may also be included.

Topical anesthetics and astringents such as pramoxine, lidocaine, and zinc sulfate; antihistamines including diphenhydramine hydrochloride and doxepin; antibiotics including polymyxin B, neomycin, clindamycin, benzoyl peroxide, erythromycin, minocycline tetracycline; antibacterial and antifungals, including triclosan, mupirocin, zinc sulfate, sulfur and pyrithione zinc; topical analgesics including salycylates (aspirin) and NSAIDS (ibuprofen, naproxen) as well as cox-2 inhibitors are all suitable components of the improved composition.

Flavonoids have potent anti-inflammatory as well as antioxidant, antimicrobial and anti-mitotic properties. Suitable flavonoids include epicatechins, guercetin, proanthocyanidins, epicatechinshersperidin methyl chalcone, soy isoflavin, and genestein. Soy isoflavone mixtures including genistein, daidzein and glycitein have been found to be safe for human use.

Quercetin is a flavonoid that forms the 'backbone' for several other flavonoids, including the citrus flavonoids rutin, hesperidin, haringin and tangeritin. Quercetin, thought to be the most active of the flavonoids, has demonstrated significant anti-inflammatory activity by inhibiting both the manufacture and release of histamine and other allergic/inflammatory mediators. It further exhibits potent antioxidant activity and Vitamin C sparing action. Hesperidin methyl chalcone is known for stabilizing capillary membranes and reducing permeability, thereby reducing redness and swelling related to inflammation at the base of hair follicles.

Proanthocyanidins extracts demonstrate a wide range of pharmacological activity, including increasing intracellular Vitamin C levels, decreasing capillary permeability and fragility, scavenging oxidants and free radicals, and inhibiting destruction of collagen, the most abundant protein in the body.

Epicatechin improves blood flow. Cocoa, particularly dark chocolate, contains significant levels of epicatechin and has been found to have nearly twice the antioxidant content of red wine, and up to three times that of green tea.

Cell growth inhibitors, for example nordihydroguaretic acid, a topical inhibitor of DHT (Dihydroepitestosterone), help prevent or treat follicular acne via an anti-hormonal pathway. Additionally, soluble fiber sources such as oat beta glucan may further be included.

The improved composition of the present invention may further include non-active ingredients well known in the art, including surfactants, preservatives, excipients, gelling agents, fragrances, buffers, binders, emulsifiers, solvents, electrolytes, sebum absorbing polymers and other polymers, pigments, sunblocking and sunscreening agents, physical exfoliating particles, liposomes and chelators.

In an illustrative example, a suitable carrier is formulated, as is well known in the art, after which the active ingredients, including buffered glycolic acid, urea and tea extract or extracts are added. Suitable carriers include emulsions, creams, lotions, ointments, serums, liquids, lacquers, gels, sprays, exfoliating particulates, cleansing agents, cosmetics agents, bath additives, oils, nanosized particulates or liposomes, fragrances, powders, muds and masks.

In an illustrative embodiment utilizing green tea extract, the improved composition is applied topically to areas affected by KP at least once, preferably at least once or twice daily until improvement is observed, and then at least once or twice daily to maintain the improvement. It is anticipated that further study of the improved composition utilizing white tea extract or a mixture of green tea and white tea extracts will demonstrate even more efficacy than that of the illustrative example shown hereinbelow.

EXAMPLE

TABLE 1

An Illustrative Example of the Improved Composition for Treating KP using Green Tea Extract

| Raw Materials | Wt/wt % |
| --- | --- |
| Deionized water | 40.95 |
| Glycolic acid (and) sodium glycolate | 16.00 |
| C12-15 alkyl benzoate | 6.0 |
| Glyceryl stearate (and) PEG-100 stearate | 6.0 |
| Japanese green tea extract | 5.0 |
| Urea | 5.0 |
| Sorbitol | 5.0 |
| Hexyl laurate | 4.0 |
| C12-20 acid PEG 8 ester | 3.5 |
| Sorbitan stearate | 3.5 |
| Cetyl recinoleate | 2.0 |
| Dimethicone | 1.0 |
| Biosaccharide Gum-1 | 0.5 |
| Sodium hyaluronate | 0.5 |

TABLE 1-continued

An Illustrative Example of the Improved Composition for Treating KP using Green Tea Extract

| Raw Materials | Wt/wt % |
|---|---|
| Algae extract | 0.5 |
| Magnesium aluminum silicate | 0.2 |
| Xanthan gum | 0.2 |
| Methylparaben | 0.1 |
| Propylparaben | 0.05 |

The magnesium aluminum silicate was dispersed in the deionized water and heated to 75° C. The sorbitol and xanthan gum were then added to the heated mixture to form the water phase.

The hexyl laurate, C12-15 alkyl benzoate, C12-20 acid PEG-8 ester, cetyl ricinoleate, glyceryl stearate and PEG-100 stearate, sorbitan stearate, methylparaben, propylparaben and dimethicone were combined and heated to 75° C. to form the oil phase. The water and oil phases were combined and allowed to cool under constant stirring. When the temperature reached 45° C., the buffered glycolic acid containing sodium glycolate was added, followed by the remaining components. The resulting composition was continually stirred until reaching room temperature, forming a cream having pH of 4.0 to 5.0 at 25° C., and having a viscosity of 20,000 to 40,000 cps RVT, TC, 10 rpm.

The resulting cream was tested to determine the ability of the resulting cream (hereinafter the test material) to diminish the appearance of KP by decreasing inflammation in hair follicles, increasing skin moisturization and reducing skin roughness.

Clinical Grading of Overall Keratosis Pilaris

Visual assessments for the severity of KP of the designated upper arm were performed by a study coordinator utilizing a scale for which the initiation of the line corresponds to "No Keratosis Pilaris," the center position of the line is "Moderate" and the maximum position of the line is "Severe Keratosis Pilaris."

The distance between the evaluator's mark and zero point of the scale is measured in millimeters. This allows for a quantitative assessment of the extent of changes perceived visually. Assessments of overall KP were performed utilizing the scale shown in FIG. 1.

Mediscope, FotoFinder Systems, Inc. (Clinical Digital Photography)

Mediscope combines the high resolution of digital photography with the direct capture features of a software archiving system and, in doing so, simplifies the photo documentation process. It also ensures consistent before and after photographs so that observed changes may be attributed to the use of the test material.

Mediscope utilizes a Canon Powershot G6 (7.1 Mega Pixels) camera. It takes high-resolution photographs that can be viewed immediately on-screen. The entire imaging process is controlled by the software. By selecting the appropriate image profile (portrait images, total body shots, close-ups, etc.), all camera settings are automatically adjusted. The overlay feature allows the baseline images to be overlaid onto the live preview images, thus ensuring almost exact repositioning at every visit.

The degree of erythema and inflammation was determined by grading a full-size digital image captured via Mediscope Photography.

Visual grading of digital images to determine the degree of Erythema of the designated upper arm were performed by a study coordinator utilizing a scale for which the initiation of the line corresponds to "No Redness," the center position of the line is "Moderate" and the maximum position of the line is "Severe Redness."

Visual grading of digital images to determine the degree of Inflammation of the designated upper arm were performed by a study coordinator utilizing a scale for which the initiation of the line corresponds to "Non-inflamed," the center position of the line is "Moderate" and the maximum position of the line is "Very Inflamed."

The distance between the evaluator's mark and zero point of the scale is measured in millimeters. This allows for a quantitative assessment of the extent of changes perceived visually. Assessments of Erythema and Inflammation were performed utilizing the scoring scales are also illustrated in FIG. 1.

Mediscope D-Scope II (Close-Up Images)

D-Scope 10-40 is a micro lens that permits the Investigator to take images of the skin in 40× magnification. Balanced illumination of the viewing area is guaranteed by the digital camera's flash and D-Scope's prism reflector ring and integrated LED lamps. Hair follicles, blemishes, pores, etc. can be accurately monitored at selected intervals to determine the effectiveness of the test materials.

Corneometer (Moisturization)

The Corneometer is a commercially available instrument (CM-820, Courage and Khazaka, Germany), which is designed to measure changes in the capacitance of the skin resulting from changes in the degree of hydration. The Corneometer expresses the capacitance of the skin in arbitrary units of skin hydration (H) and is particularly sensitive to low hydration levels. This instrument is capable of measuring the moisture of the stratum corneum to a depth of 0.1 mm and has been used to measure the effects of cosmetic preparations on the moisture content of the skin.

Image Analysis of Silflo™ Replicas (Large Rings)

The texture of the skin can be assessed by making negative impressions of the skin. Skin replicas are made by placing Silflo™ impression material against the sampling area, positioned with Replica™ locating rings. Replicas are made in the same manner for all subjects by positioning the locating ring, filled with Silflo™ paste, in consistent alignment for every sample taken during the study period. The technician measured from the subject's elbow to the center of the arm and positioned the Replica locating ring at the designated site. The resultant replicas can be evaluated by a technique that combines image analysis and surface shadowing under grazing illumination.

The replicas are illuminated at a precisely defined angle to create shadows that are analyzed according to shades of gray. A number of variables are determined that characterize the shadows of the replica. These variables assess diameter, height, shadow area and count. Each replica is analyzed, as explained in FIGS. 2 and 3—Keratosis Pilaris Analysis Method. Treatment effects of a test material on skin texture parameters can be examined by evaluating the variables determined for treated and untreated skin.

Panel Selection

Eighteen male and female subjects (5 males and 13 females), ranging in age from 13 to 63 years, were impaneled for study participation.

Test Method

For each subject, either the right or the left upper arm was selected for the clinical grading of Overall Keratosis Pilaris. A CRL technician determined the selection of the designated arm based on the severity of KP. For all subjects, the designated arm was utilized for the clinical grading of Overall Keratosis Pilaris, Mediscope Photography, Mediscope D-Scope II Imaging and Image Analysis of Silflo™ Replicas. For these evaluations, arm selection remained consistent throughout the study period. Corneometer measurements were taken from either the right or left upper arm, in accordance with a computer-generated randomization code. For the baseline and 30-minute post-application Corneometer evaluations, measurements were taken from both the right and the left upper arms site locations such that the designated [randomized] upper arm represented the treated upper arm site and the contralateral upper arm served as each subject's untreated control. Although the designated upper arm was evaluated for Corneometer measurements at Week 6, the non-designated upper arm [control] test site was not measured at the 6-week interval.

The Visual Assessment of Overall Keratosis Pilaris was performed on the entire back of the designated upper arm of each subject. For each panelist, a full-size digital image was captured via Mediscope Photography and the entire back of the designated arm was photographed under the same conditions at each evaluation. Images were later clinically graded for the presence of erythema and inflammation. Mediscope D-Scope II images were captured from an area of the designated posterior upper arm of each subject exhibiting moderate KP, as selected by a CRL technician. The exact location of the imaged area was recorded on a Test Site Locator Document to ensure that the same area of skin was captured at each evaluation interval.

Silflo™ Replicas were taken from the center of the back of the designated upper arm. The technician measured from the subject's elbow to the center of the arm and positioned the Replica locating ring at the designated site. Baseline and 30-minute post-application Corneometer measurements were taken from the back of both upper arms and the center of the upper arms were marked to ensure that the same area was measured at each interval. At Week 6, Corneometer measurements were taken only from the designated upper arm of each subject, in accordance with the original randomization code. All other evaluations were performed at baseline and after 6 weeks of product use. At the conclusion of the study the Daily Diaries and any remaining test materials were collected.

Study Related Comments

Following baseline evaluations, the initial test material application was performed by each subject under the supervision of a CRL technician, as per the Sponsor's instructions. At this time, subjects applied the test material to the designated arm only. All subjects were provided with the test material, a bar of non-moisturizing soap (Aveeno® Balancing Bar) to use in place of their usual cleanser, study instructions and a Daily Diary in which to record product applications. All subjects were instructed to apply a teaspoon amount of product to each the right and the left upper arm twice daily, morning and evening, until the test material fully absorbed into the skin.

The randomization design specified in the study protocol was altered in order to have a CRL technician choose the designated upper arm site on a selected arm based on the severity of KP. That designated arm was utilized for the clinical grading of Overall Keratosis Pilaris, Mediscope Photography, Mediscope D-Scope II Imaging and Image Analysis of Silflo™ Replicas. For these evaluations, arm selection remained consistent for the duration of the study. The computer-generated randomization code was solely utilized for the Corneometer evaluations.

Statistical Methods

Paired t-test was applied to determine the differences between baseline and Week 6 for the visual assessment of overall KP, clinical grading of Mediscope photographs for erythema and inflammation and Image Analysis of Silflo™ Replica data.

One-way ANOVA was applied to determine the differences of Corneometer readings between baseline, 30 minutes and Week 6 for treated sites. If overall F-test was significant, Tukey test was applied to determine where the significant differences existed. The ANOVA test uses the F-test to determine whether there exists a significant difference among means of treatments or time intervals. When the F test rejects the null hypothesis, it is usually necessary to undertake a thorough analysis of the nature of the factor-level effects. Tukey test is a multiple comparison procedure. This is the method which examines or compares more than one pair of means or proportions at the same time but controls the overall significance level to be the same as that which is specified for a single pair comparison.

Paired t-test was applied to determine the differences of Corneometer readings between baseline and 30 minutes, baseline and Week 6 for treated sites. The same method was applied to determine the differences between baseline and 30 minutes for control sites. Comparisons of Corneometer readings between treated and control sites at 30 minutes were based on percentage change from baseline. Paired t-test was applied.

Statistical significance was declared at the 95% confidence level for all two-tailed p-values less than or equal to 0.05.

Data obtained from image analysis of Silflo™ replicas, which was performed by Bionet, Inc., were analyzed using StatSoft STATISTICA 5.5. Statistical calculations performed using Microsoft Excel 2000.

Results

Completed and Discontinued Subjects

Seventeen subjects completed the study. One subject discontinued study participation for reasons not related to the test material.

Study Data: Instrumental Measurements, Visual and Dermal Evaluations

Tables I and II list the average clinical grading of Overall Keratosis Pilaris and calculated percentage changes from baseline at the final visit. Tables III and IV list the average clinical grading of Mediscope photographs for the degree of erythema and inflammation and calculated percentage changes from baseline at the final visit. Tables V and VI lists the Image Analysis of Silflo™ Replicas and the statistical variables determined for comparisons of post-treatment measurements or scores to baseline. For all subjects, average Corneometer measurements at designated post-treatment intervals are listed for treated and control sites in Table VII. Table VIII includes comparisons of Corneometer readings between baseline and 30 minutes and baseline and Week 6 for treated sites and comparisons between baseline and 30 minutes for control sites. Table IX includes statistical analysis of percentage change from baseline at 30 minutes post-application for differences between treated and control sites. Table X includes the Tukey multiple comparison of Corneometer readings between baseline and each post-application time interval for treated sites.

CONCLUSION

Evaluations for this study consisted of clinical grading of Overall Keratosis Pilaris, Mediscope Photography, Mediscope D-Scope II Imaging, Image Analysis of Silflo™ Replicas and Corneometer measurements.

Under the conditions of this study, these evaluations demonstrated efficacy of the test material to diminish the appearance of KP by decreasing inflammation of the hair follicles and increasing skin hydration. Treatment effects that were measured with statistical significance (p≤0.05) during the 6-week study period included the following:

A Visual Analog Scale (VAS) was used (as outlined in Table I) to clinically grade full-size digital photographs which were captured utilizing Mediscope Photography. A significant improvement in overall KP was assessed, exhibiting a 31% reduction in KP. Of the panelists that completed the 6-week test phase of the study, 100% of subjects experienced some level of improvement.

Clinical grading of full-size digital photographs captured utilizing Mediscope Photography demonstrated statistically significant reductions in the degree of erythema and inflammation. Decreases in erythema were equivalent to a 20% reduction at Week 6 relative to that at baseline and decreases in inflammation were equivalent to a 19% reduction at Week 6 relative to baseline.

When comparing Comeometer readings at 30 minutes following the initial application of KP Duty, statistically significant differences were measured between treated (50%) and control (12%) upper arm test sites. Skin hydration levels were significantly higher for treated sites relative to that measured for untreated control sites.

Statistically significant increases in the hydration of the treated skin were measured at 30 minutes following the initial test material application and after 6 weeks of repeated application. Improvements in skin hydration of upper arm test sites were equivalent to 50% at 30 minutes following the initial application and 106% after 6 weeks of treatment with KP Duty.

Tukey groupings comparing Comeometer readings of treated sites between baseline and post-application time intervals demonstrated statistically significant improvements in skin hydration levels between baseline and 30 minutes post-treatment and between baseline and Week 6. Significant improvements also existed between the 30-minute interval and the 6-week interval, demonstrating increases in skin hydration at Week 6 relative to that measured at 30 minutes following the initial test material application.

As determined by Image Analysis of Silflo™ replicas, no significant improvements in skin texture were measured.

TABLE I

Clinical Grading of Overall Keratosis Pilaris

| Subject Number | Visual Analog Scale (VAS) Scores | | % Change from Baseline |
|---|---|---|---|
| | Baseline | Week 6 | Week 6 |
| 1 | 80 | 70 | −13% |
| 2 | 60 | 31 | −48% |
| 3 | 47 | 23 | −51% |
| 4 | 53 | 34 | −36% |
| 5 | 61 | 42 | −31% |
| 6 | 24 | 6 | −75% |
| 7 | 37 | 10 | −73% |
| 8 | 79 | 50 | −37% |
| 9 | 50 | 37 | −26% |
| 10 | 46 | 34 | −26% |
| 11 | 69 | 58 | −16% |
| 12 | 39 | 54 | 38% |
| 13 | 44 | 42 | −5% |
| 14 | 39 | 25 | −36% |
| 15 | 33 | 23 | −30% |
| 17 | 49 | 46 | −6% |
| 18 | 29 | 14 | −52% |
| Mean | 49 | 35 | Mean −31% |
| Std. Dev. | 16 | 17 | Std. Dev. 27% |

TABLE II

Statistical Analysis of Clinical Grading of Overall Keratosis Pilaris

| | Visual Analog Scale (VAS) Scores | |
|---|---|---|
| | Baseline | Week 6 |
| Mean | 49 | 35 |
| Variance | 263 | 305 |
| Observations | 17 | 17 |
| Pearson Correlation | 0.79 | |
| Hypothesized Mean Difference | 0 | |
| Df | 16 | |
| t Stat | 5.29 | |
| P(T <= t) one-tail | 3.67E−05 | |
| t Critical one-tail | 1.75 | |
| P(T <= t) two-tail | 7.34E−05 | |
| t Critical two-tail | 2.12 | |

TABLE III

Clinical Grading of Mediscope Photographs

| Subject Number | Baseline | Week 6 | % Change from Baseline Week 6 |
|---|---|---|---|
| Erythema | | | |
| 1 | 69 | 50 | −28% |
| 2 | 47 | 25 | −47% |
| 3 | 30 | 14 | −53% |
| 4 | 68 | 20 | −71% |
| 5 | 50 | 18 | −64% |
| 6 | 28 | 9 | −68% |
| 7 | 22 | 16 | −27% |
| 8 | 52 | 51 | −2% |
| 9 | 50 | 50 | 0% |
| 10 | 37 | 36 | −3% |
| 11 | 50 | 50 | 0% |
| 12 | 25 | 40 | 60% |
| 13 | 36 | 25 | −31% |
| 14 | 34 | 30 | −12% |
| 15 | 18 | 22 | 22% |
| 17 | 50 | 53 | 6% |
| 18 | 12 | 10 | −17% |
| Mean | 40 | 31 | Mean −20% |
| Std. Dev. | 16 | 16 | Std. Dev. 35% |
| Inflammation | | | |
| 1 | 59 | 38 | −36% |
| 2 | 50 | 18 | −64% |
| 3 | 21 | 12 | −43% |
| 4 | 25 | 4 | −84% |
| 5 | 50 | 19 | −62% |
| 6 | 18 | 7 | −61% |
| 7 | 12 | 13 | 8% |
| 8 | 47 | 47 | 0% |
| 9 | 53 | 54 | 2% |
| 10 | 27 | 24 | −11% |
| 11 | 26 | 20 | −23% |

TABLE III-continued

Clinical Grading of Mediscope Photographs

| Subject Number | Baseline | Week 6 | | % Change from Baseline Week 6 |
|---|---|---|---|---|
| 12 | 12 | 16 | | 33% |
| 13 | 30 | 39 | | 30% |
| 14 | 16 | 17 | | 6% |
| 15 | 24 | 22 | | −8% |
| 17 | 50 | 50 | | 0% |
| 18 | 15 | 14 | | −7% |
| Mean | 31 | 24 | Mean | −19% |
| Std. Dev. | 16 | 15 | Std. Dev. | 34% |

TABLE IV

Statistical Analysis of Clinical Grading of Mediscope Photographs

| | Baseline | Week 6 |
|---|---|---|
| | Erythema Visual Analog Scale (VAS) Scores | |
| Mean | 40 | 31 |
| Variance | 271 | 247 |
| Observations | 17 | 17 |
| Pearson Correlation | 0.55 | |
| Hypothesized Mean Difference | 0 | |
| Df | 16 | |
| t Stat | 2.53 | |
| P(T <= t) one-tail | 1.13E−02 | |
| t Critical one-tail | 1.75 | |
| P(T <= t) two-tail | 2.25E−02 | |
| t Critical two-tail | 2.12 | |
| | Inflammation Visual Analog Scale (VAS) Scores | |
| Mean | 31 | 24 |
| Variance | 263 | 236 |
| Observations | 17 | 17 |
| Pearson Correlation | 0.71 | |
| Hypothesized Mean Difference | 0 | |
| Df | 16 | |
| t Stat | 2.42 | |
| P(T <= t) one-tail | 1.40E−02 | |
| t Critical one-tail | 1.75 | |
| P(T <= t) two-tail | 2.79E−02 | |
| t Critical two-tail | 2.12 | |

TABLE V

Image Analysis of Silflo ™ Replicas

| Subject Number | Baseline | Week 6 | | % Change from Baseline Week 6 |
|---|---|---|---|---|
| | Diameter | | | |
| 1 | 1.2421 | 1.2783 | | 3% |
| 2 | 1.3398 | 1.3349 | | 0% |
| 3 | 1.0356 | 1.2852 | | 24% |
| 4 | 1.3430 | 1.6262 | | 21% |
| 5 | 1.2153 | 1.2944 | | 7% |
| 6 | 1.4634 | 1.7111 | | 17% |
| 7 | 0.9996 | 1.0032 | | 0% |
| 8 | 1.2006 | 1.1650 | | −3% |
| 9 | 1.3691 | 1.1866 | | −13% |
| 10 | 1.3651 | 1.2020 | | −12% |
| 11 | 1.2261 | 1.1102 | | −9% |
| 12 | 1.2069 | 1.3106 | | 9% |
| 13 | 1.1804 | 1.1299 | | −4% |
| 14 | 1.5857 | 1.1650 | | −27% |
| 15 | 1.1899 | 1.4455 | | 21% |
| 17 | 1.4325 | 1.2343 | | −14% |
| 18 | 1.3052 | 1.2591 | | −4% |
| Mean | 1.2765 | 1.2789 | Mean | 1% |
| Std. Dev. | 0.1479 | 0.1784 | Std. Dev. | 14% |
| | Height | | | |
| 1 | 0.8708 | 0.8199 | | −6% |
| 2 | 0.8072 | 0.8760 | | 9% |
| 3 | 0.7596 | 0.7642 | | 1% |
| 4 | 0.9214 | 1.0306 | | 12% |
| 5 | 0.8921 | 0.8910 | | 0% |
| 6 | 0.8165 | 0.7621 | | −7% |
| 7 | 0.7179 | 0.7828 | | 9% |
| 8 | 0.8963 | 0.8301 | | −7% |
| 9 | 0.8477 | 0.8846 | | 4% |
| 10 | 0.8378 | 0.7955 | | −5% |
| 11 | 0.8404 | 0.8241 | | −2% |
| 12 | 0.9227 | 0.8467 | | −8% |
| 13 | 0.8975 | 0.8989 | | 0% |
| 14 | 0.8579 | 0.8693 | | 1% |
| 15 | 0.8376 | 0.8295 | | −1% |
| 17 | 0.7887 | 0.8416 | | 7% |
| 18 | 0.8479 | 0.9260 | | 9% |
| Mean | 0.8447 | 0.8513 | Mean | 1% |
| Std. Dev. | 0.0555 | 0.0660 | Std. Dev. | 6% |
| | Shadow Area | | | |
| 1 | 0.8727 | 0.8226 | | −6% |
| 2 | 0.8413 | 0.8826 | | 5% |
| 3 | 0.6761 | 0.7459 | | 10% |
| 4 | 1.0438 | 1.1439 | | 10% |
| 5 | 0.8584 | 0.8913 | | 4% |
| 6 | 0.8982 | 0.9661 | | 8% |
| 7 | 0.6295 | 0.6266 | | 0% |
| 8 | 0.8374 | 0.7412 | | −11% |
| 9 | 0.8508 | 0.8504 | | 0% |
| 10 | 0.8825 | 0.7518 | | −15% |
| 11 | 0.7960 | 0.7011 | | −12% |
| 12 | 0.8806 | 0.8620 | | −2% |
| 13 | 0.8329 | 0.8037 | | −4% |
| 14 | 1.0404 | 0.7685 | | −26% |
| 15 | 0.7861 | 0.9231 | | 17% |
| 17 | 0.9006 | 0.8151 | | −9% |
| 18 | 0.8418 | 0.8959 | | 6% |
| Mean | 0.8511 | 0.8348 | Mean | −1% |
| Std. Dev. | 0.1024 | 0.1176 | Std. Dev. | 11% |
| | Count | | | |
| 1 | 21 | 8 | | −62% |
| 2 | 20 | 8 | | −60% |
| 3 | 9 | 7 | | −22% |
| 4 | 8 | 8 | | 0% |
| 5 | 18 | 17 | | −6% |
| 6 | 18 | 16 | | −11% |
| 7 | 9 | 6 | | −33% |
| 8 | 20 | 10 | | −50% |
| 9 | 13 | 18 | | 38% |
| 10 | 11 | 14 | | 27% |
| 11 | 18 | 26 | | 44% |
| 12 | 17 | 16 | | −6% |
| 13 | 21 | 24 | | 14% |
| 14 | 4 | 11 | | 175% |
| 15 | 13 | 24 | | 85% |
| 17 | 15 | 14 | | −7% |
| 18 | 12 | 11 | | −8% |
| Mean | 15 | 14 | Mean | 7% |
| Std. Dev. | 5 | 6 | Std. Dev. | 58% |

TABLE VI

Statistical Variables of Image Analysis of Silflo ™ Replicas

|  | Baseline | Week 6 |
|---|---|---|
| | Diameter | |
| | % Change | |
| | from Baseline | |
| Mean | 1.2765 | 1.2789 |
| Variance | 0.0219 | 0.0318 |
| Observations | 17 | 17 |
| Pearson Correlation | 0.33 | |
| Hypothesized Mean Difference | 0 | |
| Df | 16 | |
| t Stat | −0.05 | |
| P(T <= t) one-tail | 0.48 | |
| t Critical one-tail | 1.75 | |
| P(T <= t) two-tail | 0.96 | |
| t Critical two-tail | 2.12 | |
| | Height | |
| | % Change | |
| | from Baseline | |
| Mean | 0.8447 | 0.8513 |
| Variance | 0.0031 | 0.0044 |
| Observations | 17 | 17 |
| Pearson Correlation | 0.60 | |
| Hypothesized Mean Difference | 0 | |
| Df | 16 | |
| t Stat | −0.50 | |
| P(T <= t) one-tail | 0.31 | |
| t Critical one-tail | 1.75 | |
| P(T <= t) two-tail | 0.63 | |
| t Critical two-tail | 2.12 | |
| | Shadow Area | |
| | % Change | |
| | from Baseline | |
| Mean | 0.8511 | 0.8348 |
| Variance | 0.0105 | 0.0138 |
| Observations | 17 | 17 |
| Pearson Correlation | 0.60 | |
| Hypothesized Mean Difference | 0 | |
| Df | 16 | |
| t Stat | 0.67 | |
| P(T <= t) one-tail | 0.26 | |
| t Critical one-tail | 1.75 | |
| P(T <= t) two-tail | 0.51 | |
| t Critical two-tail | 2.12 | |
| | Count | |
| | % Change | |
| | from Baseline | |
| Mean | 15 | 14 |
| Variance | 27 | 40 |
| Observations | 17 | 17 |
| Pearson Correlation | 0.34 | |
| Hypothesized Mean Difference | 0 | |
| Df | 16 | |
| t Stat | 0.33 | |
| P(T <= t) one-tail | 0.37 | |
| t Critical one-tail | 1.75 | |
| P(T <= t) two-tail | 0.75 | |
| t Critical two-tail | 2.12 | |

TABLE VII

Corneometer Measurements

| Subject Number | Corneometer - Treated Designated Upper Arm Sites | | | % Change from Baseline | |
|---|---|---|---|---|---|
| | Baseline | 30 Minutes | Week 6 | 30 Minutes | Week 6 |
| 1 | 29 | 31 | 65 | 7% | 124% |
| 2 | 35 | 50 | 69 | 43% | 97% |
| 3 | 35 | 56 | 56 | 60% | 60% |
| 4 | 32 | 35 | 48 | 9% | 50% |
| 5 | 17 | 18 | 47 | 6% | 176% |
| 6 | 24 | 36 | 65 | 50% | 171% |
| 7 | 21 | 31 | 52 | 48% | 148% |
| 8 | 26 | 47 | 49 | 81% | 88% |
| 9 | 20 | 43 | 48 | 115% | 140% |
| 10 | 23 | 41 | 52 | 78% | 126% |
| 11 | 22 | 29 | 70 | 32% | 218% |
| 12 | 19 | 39 | 29 | 105% | 53% |
| 13 | 22 | 44 | 55 | 100% | 150% |
| 14 | 23 | 27 | 24 | 17% | 4% |
| 15 | 29 | 37 | 28 | 28% | −3% |
| 17 | 19 | 26 | 43 | 37% | 126% |
| 18 | 23 | 29 | 39 | 26% | 70% |
| Mean | 25 | 36 | 49 | Mean 50% | 106% |
| Std. Dev. | 6 | 10 | 14 | Std. Dev. 35% | 61% |

| Subject Number | Skin Hydration (H) Control Sites | | % Change from Baseline |
|---|---|---|---|
| | Baseline | 30 Minutes | 30 Minutes |
| 1 | 30 | 30 | 0% |
| 2 | 30 | 36 | 20% |
| 3 | 37 | 34 | −8% |
| 4 | 27 | 41 | 52% |
| 5 | 22 | 24 | 9% |
| 6 | 23 | 20 | −13% |
| 7 | 19 | 20 | 5% |
| 8 | 29 | 30 | 3% |
| 9 | 20 | 15 | −25% |
| 10 | 24 | 25 | 4% |
| 11 | 26 | 22 | −15% |
| 12 | 14 | 19 | 36% |
| 13 | 23 | 26 | 13% |
| 14 | 25 | 28 | 12% |
| 15 | 33 | 24 | −27% |
| 17 | 20 | 35 | 75% |
| 18 | 31 | 48 | 55% |
| Mean | 25 | 28 | Mean 12% |
| Std. Dev. | 6 | 9 | Std. Dev. 29% |

TABLE VIII

Statistical Analysis of Corneometer Measurements between Intervals

| | Treated Sites Comparison of Corneometer Readings Between Baseline and 30 Minutes | |
|---|---|---|
| | Baseline | 30 Minutes |
| Mean | 25 | 36 |
| Variance | 30 | 95 |
| Observations | 17 | 17 |
| Pearson Correlation | 0.61 | |
| Hypothesized Mean Difference | 0 | |
| Df | 16 | |
| t Stat | −6.25 | |
| P(T <= t) one-tail | 5.77E−06 | |
| t Critical one-tail | 1.75 | |
| P(T <= t) two-tail | 1.15E−05 | |
| t Critical two-tail | 2.12 | |

TABLE VIII-continued

Statistical Analysis of Corneometer Measurements between Intervals

Treated Sites
Comparison of Corneometer Readings Between Baseline and Week 6

| | Baseline | Week 6 |
|---|---|---|
| Mean | 25 | 49 |
| Variance | 30 | 191 |
| Observations | 17 | 17 |
| Pearson Correlation | 0.31 | |
| Hypothesized Mean Difference | 0 | |
| Df | 16 | |
| t Stat | −7.71 | |
| P(T <= t) one-tail | 4.49E−07 | |
| t Critical one-tail | 1.75 | |
| P(T <= t) two-tail | 8.98E−07 | |
| t Critical two-tail | 2.12 | |

Control Sites
Comparison of Corneometer Readings Between Baseline and 30 Minutes

| | Baseline | 30 Minutes |
|---|---|---|
| Mean | 25 | 28 |
| Variance | 34 | 74 |
| Observations | 17 | 17 |
| Pearson Correlation | 0.56 | |
| Hypothesized Mean Difference | 0 | |
| Df | 16 | |
| t Stat | −1.49 | |
| P(T <= t) one-tail | 0.08 | |
| t Critical one-tail | 1.75 | |
| P(T <= t) two-tail | 0.16 | |
| t Critical two-tail | 2.12 | |

TABLE IX

Statistical Analysis of Corneometer Measurements

Skin Hydration (H) % Change from Baseline at 30 minutes post-application

| | Treated | Control |
|---|---|---|
| Mean | 50% | 12% |
| Variance | 12% | 8% |
| Observations | 17 | 17 |
| Pearson Correlation | −0.20 | |
| Hypothesized Mean Difference | 0 | |
| Df | 16 | |
| t Stat | 3.16 | |
| P(T <= t) one-tail | 3.04E−03 | |
| t Critical one-tail | 1.75 | |
| P(T <= t) two-tail | 6.08E−03 | |
| t Critical two-tail | 2.12 | |

TABLE X

Statistical Analysis of Corneometer Measurements Comparison of Corneometer Readings between Baseline and Post-Application Time Intervals

| Tukey Grouping | Mean | N | Visit |
|---|---|---|---|
| A | 49 | 17 | Week 6 |
| B | 36 | 17 | 30 Minutes |
| C | 25 | 17 | Baseline |

Significant differences existed between all time intervals (baseline, 30 minutes post-application and Week 6). Skin hydration levels were significantly higher at 30 minutes post-treatment and at Week 6 relative to that at baseline. Significant differences existed between the 30 minute post-application interval and the Week 6 interval, demonstrating an increase in the hydration of the skin at Week 6 relative to the 30 minute post-application time interval.
* Means with the same letter are not significantly different.

Having described the invention in detail, those skilled in the art will appreciate that modifications may be made of the invention without departing from its spirit and scope. Therefore, it is not intended that the scope of the invention be limited to the specific embodiments described. Rather, it is intended that the appended claims and their equivalents determine the scope of the invention.

I claim:

1. A composition for treating keratosis pilaris, wherein the composition comprises:
   from about 0.01% to 60% buffered glycolic acid;
   from about 0.01% to 50% urea;
   from about 0.01% to 30.0% salicylic acid;
   from about 0.01% to 30.0% azelaic acid;
   from about 0.01% to 30.0% lactic acid; and
   at least 0.01% of a tea extract selected from the group consisting of white tea extract and a mixture consisting of white tea extract and green tea extract.

2. The composition of claim 1, wherein the composition further comprises at least one skin lightening agent.

3. The composition of claim 2, wherein the at least one skin lightening agent is a skin lightening agent selected from the group consisting of alpha hydroxy acids, beta hydroxy acids, Vitamin A, Vitamin A derivatives, sutilains, tyrosinase receptor blockers, Vitamin C, Vitamin C derivatives, melanin inhibitors and mixtures thereof.

4. The composition of claim 3, wherein the Vitamin A derivatives is a Vitamin A derivative selected from the group consisting of tretinoin, iso-treninoin, retinol, retinyl palmitate, retinoic acid, tazarotene, adapalene and mixtures thereof.

5. The composition of claim 1, wherein the composition further comprises at least one component selected from the group consisting of organic acids, herbs, vitamins, minerals, steroidal compounds, essential oils, immunosuppressants, topical anesthetics, tyronase inhibitors, antihistamines, antibiotics, antibacterials, antifungals, flavinoids, analgesics, soluble fiber and mixtures thereof.

6. A composition for treating keratosis pilaris, wherein the composition comprises:
   from about 5% to 20% buffered glycolic acid;
   from about 1% to 10% urea;
   from about 0.1% to 5% salicylic acid;
   from about 0.1% to 5% azelaic acid;
   from about 0.1% to 5% lactic acid; and
   at least 1% of a tea extract selected from the group consisting of white tea extract and a mixture consisting of white tea extract and green tea extract.

7. The composition of claim 6, wherein said composition further comprises at least one skin lightening agent.

8. The composition of claim 7, wherein the at least one skin lightening agent is a skin lightening agent selected from the group consisting of alpha hydroxy acids, beta hydroxy acids, Vitamin A, Vitamin A derivatives, sutilains, tyrosinase receptor blockers, Vitamin C, Vitamin C derivatives, melanin inhibitors and mixtures thereof.

9. The composition of claim 8, wherein the Vitamin A derivatives comprise a Vitamin A derivative selected from the group consisting of tretinoin, iso-treninoin, retinol, retinyl palmitate, retinoic acid, tazarotene, adapalene and mixtures thereof.

10. The composition of claim 6, further comprising at least one component selected from the group consisting of organic acids, herbs, vitamins, minerals, steroidal compounds, essential oils, immunosuppressants, topical anesthetics, tyronase inhibitors, antihistamines, antibiotics, antibacterials, antifungals, flavinoids, analgesics, soluble fiber and mixtures thereof.

11. A composition for treating keratosis pilaris, wherein the composition comprises:
   about 12% buffered glycolic acid;
   about 5% urea;
   about 2% salicylic, acid;
   about 1% azelaic acid;
   about 3% lactic acid; and
   about 5% of a tea extract selected from the group consisting of white tea extract and a mixture consisting of white tea extract and green tea extract.

12. The composition of claim 11, further comprising at least one skin lightening agent.

13. The composition of claim 12, wherein the at least one skin lightening agent comprises a skin lightening agent selected from the group consisting of alpha hydroxy acids, beta hydroxy acids, Vitamin A, Vitamin A derivatives, sutilains, tyrosinase receptor blockers, Vitamin C, Vitamin C derivatives, melanin inhibitors and mixtures thereof.

14. The composition of claim 13, wherein the Vitamin A derivatives comprise a Vitamin A derivative selected from the group consisting of tretinoin, iso-treninoin, retinol, retinyl palmitate, retinoic acid, tazarotene, adapalene and mixtures thereof.

15. The composition of claim 12, further comprising at least one component selected from the group consisting of organic acids, herbs, vitamins, minerals, steroidal compounds, essential oils, immunosuppressants, topical anesthetics, tyronase inhibitors, antihistamines, antibiotics, antibacterials, antifungals, flavonoids, analgesics, soluble fiber and mixtures thereof.

* * * * *